United States Patent [19]

Wilkins

[11] Patent Number: 5,137,521
[45] Date of Patent: Aug. 11, 1992

[54] TELESCOPING SAFETY GUARD FOR HYPODERMIC NEEDLES AND THE LIKE

[75] Inventor: John F. Wilkins, Lanoka Harbor, N.J.

[73] Assignee: Alco Machine & Tool, Inc., Bloomfield, N.J.

[21] Appl. No.: 746,861

[22] Filed: Aug. 19, 1991

[51] Int. Cl.⁵ ............................................. A61M 5/32
[52] U.S. Cl. .................................. 604/198; 604/263
[58] Field of Search .......... 604/192, 263, 198, 187, 604/110

[56] References Cited

U.S. PATENT DOCUMENTS

| | | | |
|---|---|---|---|
| 4,737,144 | 4/1988 | Choksi | 604/198 |
| 4,911,693 | 3/1990 | Paris | 604/192 |
| 4,923,447 | 5/1990 | Morgan | 604/198 |
| 4,932,940 | 6/1990 | Walker et al. | 604/110 |
| 4,935,016 | 6/1990 | Deleo | 604/263 X |
| 4,994,045 | 2/1991 | Ranford | 604/198 |

Primary Examiner—John D. Yasko
Attorney, Agent, or Firm—Louis Weinstein

[57] ABSTRACT

A safety shield slidably mounted upon a disposable hypodermic syringe and needle assembly and having an elongated guide slot which cooperates with a resilient tab cooperating therewith to maintain orientation between the syringe body and the telescoping shield. A resilient locking tab integral with the syringe body cooperates with a pair of spaced slots arranged along the telescoping shield to define the initial shielded position and the usable position respectively. The telescoping shield includes a shoulder which receives the bent-over flexible tab to lock the shield in the shielded position to prevent contact with the needle, facilitating safe handling of the assembly.

11 Claims, 4 Drawing Sheets

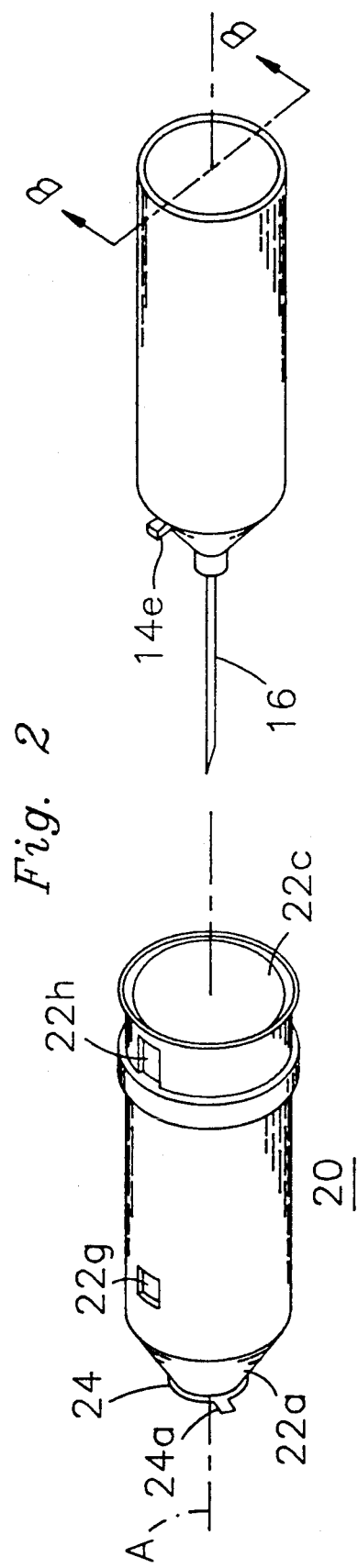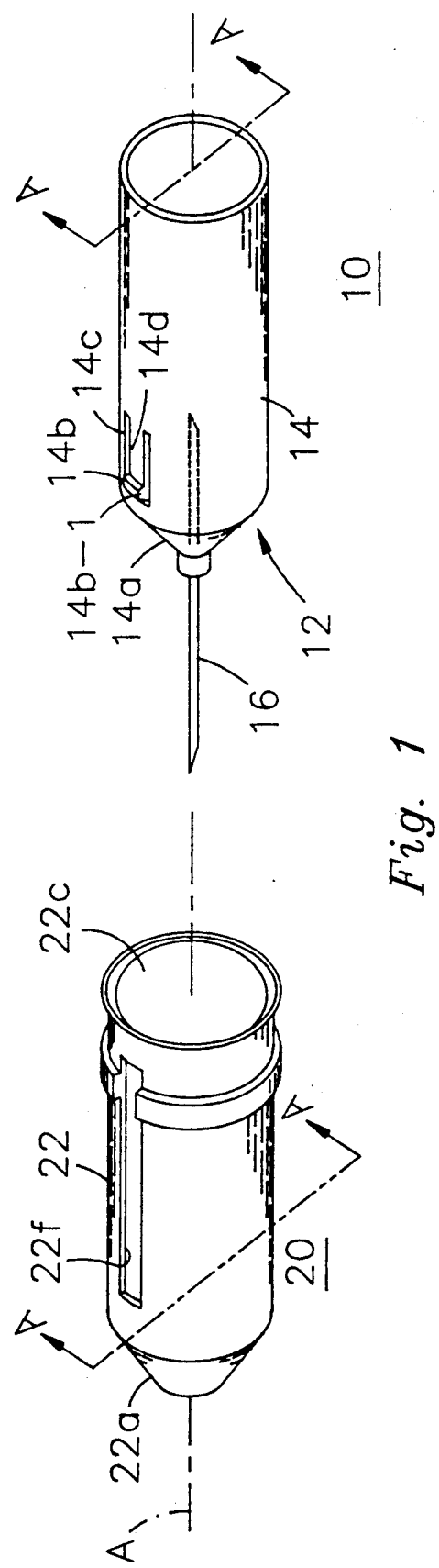

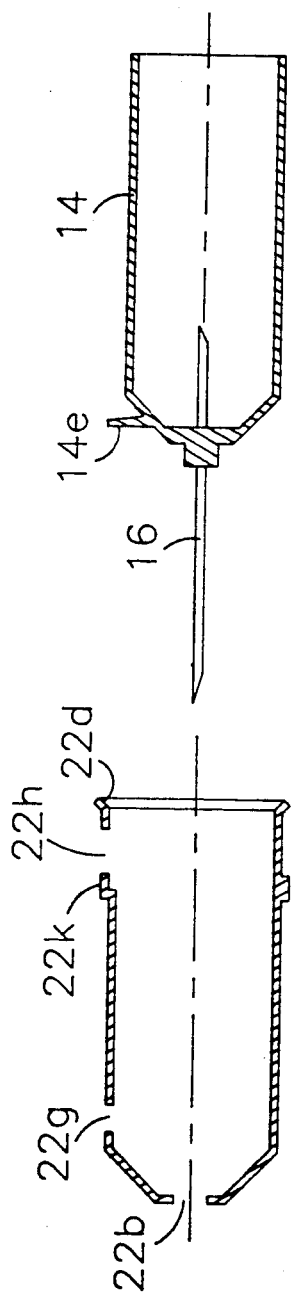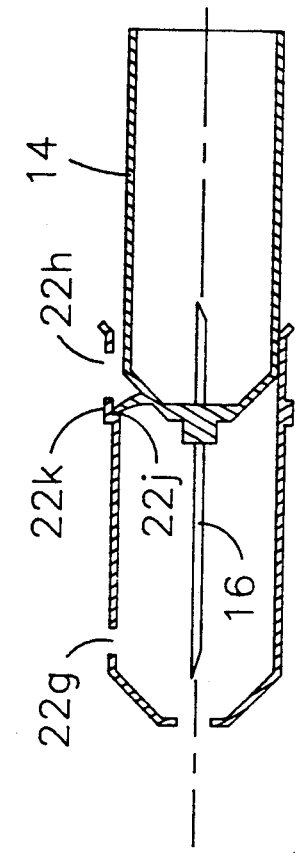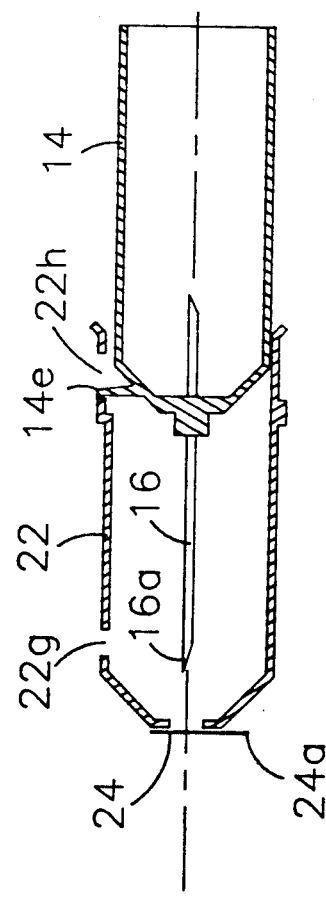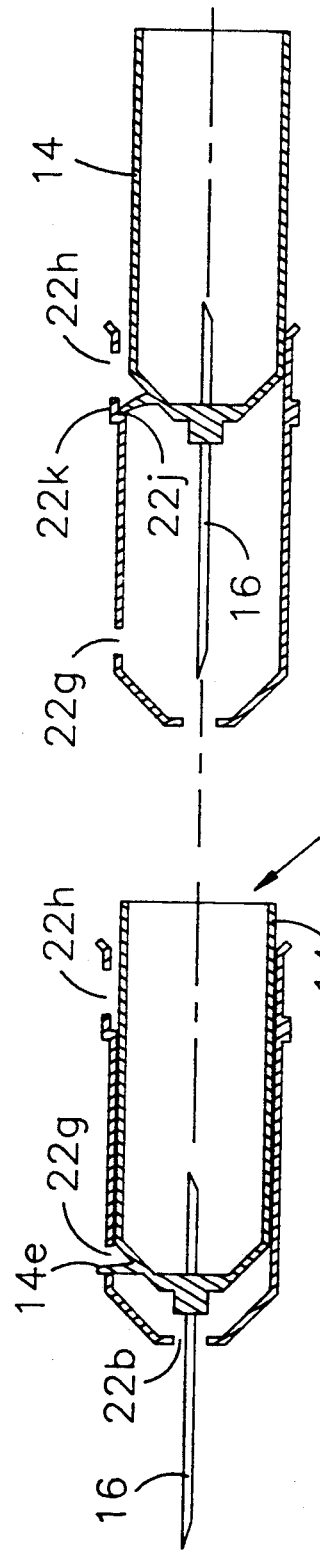
Fig. 4a
Fig. 4b
Fig. 4c
Fig. 4d

TELESCOPING SAFETY GUARD FOR HYPODERMIC NEEDLES AND THE LIKE

FIELD OF THE INVENTION

The present invention relates to shields for hypodermic needles and the like and more particularly to a novel telescoping shield movable between a shielding and exposed position and further including a flexible locking tab for locking the telescoping shield into the needle shielding position after use of the disposable hypodermic needle assembly.

BACKGROUND OF THE INVENTION

It is important to exercise proper care in the handling of hypodermic needles which includes not only handling, but use and disposal as well. The danger of injury due to being pierced by a needle is further compounded by the possible danger of infection or a resulting illness from any microbe, germ or other matter carried by the needle. In addition, it is important to prevent reuse of disposed needles which have initially been used on patients and especially those having highly contagious and even fatal diseases.

It is known in the art to protect against injury from a hypodermic needle preparatory to use. However, these shields are typically disposed of after removal from the hypodermic needle preparatory to use of the hypodermic assembly. Thus, no means are available for protecting against injury from the needle after use when disposed. Some shields have been provided which may be mounted upon the syringe to cover the needle after use. However, although these devices will protect against accidental injury, they are not capable of preventing the shield from being moved to a position to expose the needle after use and preparatory to disposal.

BRIEF DESCRIPTION OF THE INVENTION

The present invention is characterized by comprising a novel, cooperating hypodermic syringe assembly and shield which is telescopingly mounted upon the syringe assembly. The shield is provided with at least one elongated guide slot which cooperates with a resilient guide tab arranged along the syringe assembly to permit the telescoping shield to be moved between the needle shielding and needle exposed position, preparatory to use. An integral resilient locking tab extends generally radially outwardly from the hypodermic syringe and cooperates with mating openings arranged at spaced longitudinal intervals along the telescoping shield to identify the respective needle shielding and needle exposed positions. A shoulder is provided in the telescoping shield adjacent one of said position openings and is adapted to seat the locking tab in the flexed position to prevent the telescoping shield to be moved to the position exposing said needle after use of the needle. Thus, the telescoping shield serves as both the initial and final means for shielding the hypodermic syringe needle respectively preparatory to and subsequent to the use thereof without any need for removing the telescoping shield from the hypodermic syringe assembly regardless of the function to be performed.

OBJECTS OF THE INVENTION AND BRIEF DESCRIPTION OF THE FIGURES

It is, therefore, one object of the invention to provide a novel cooperating hypodermic needle assembly and telescoping shield for protecting the needle from damage and for protecting users from injury both preparatory and subsequent to use.

Still another object of the present invention is to provide a novel hypodermic syringe assembly and cooperating telescoping shield which is movable between a first position for shielding the needle preparatory to use and a second position for exposing the needle for use and which may again be retracted to the needle shielding position to protect people handling the assembly from injury.

Still another object of the present invention is to provide a novel hypodermic syringe assembly and cooperating telescoping shield movable between a needle shielding position and a needle exposing position and wherein said hypodermic syringe is provided with locking tab means cooperating with a shoulder in said telescoping shield for locking the telescoping shield in the shielding position and for preventing the shield from being moved to the needle exposing position.

The above, as well as other objects of the present invention will become apparent when reading the accompanying description and drawings in which:

FIG. 1 shows an exploded perspective view of the hypodermic syringe assembly and cooperating telescoping shield embodying the principles of the present invention;

FIG. 2 shows the assembly of FIG. 1 rotated through a predetermined angle sufficient to expose other cooperating elements of the assembly;

FIG. 4a shows a sectional view of the assembly of FIG. 2 looking in the direction of arrows B—B; and FIGS. 4b, 4c and 4d respectively show sectional views similar to that shown in FIG. 4a with the elements thereof in the needle shielding, needle exposing and needle shielding positions with the arrangement of FIG. 4d showing the locking tab in the locked position.

DETAILED DESCRIPTION OF THE INVENTION

Figure 2A:
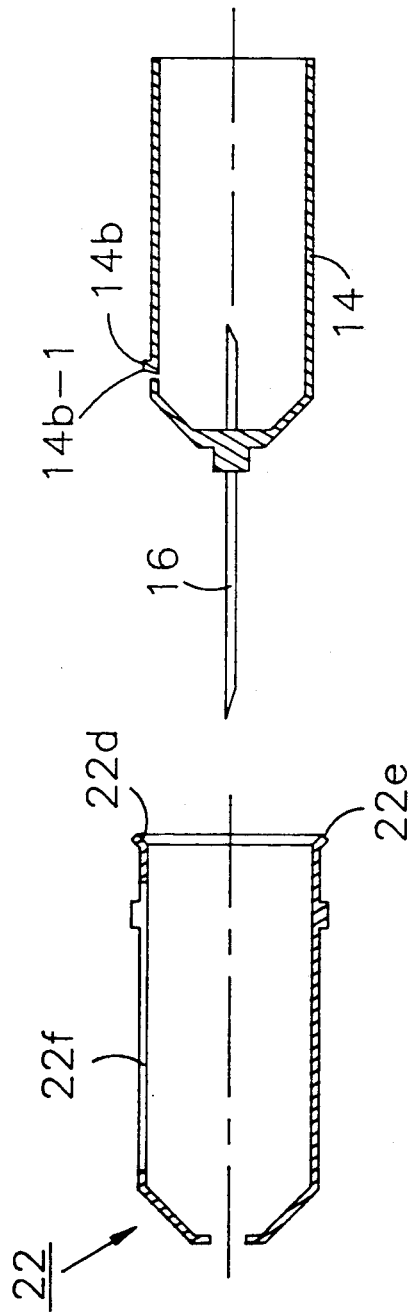
FIG. 2a shows a sectional view of the assembly of FIG. 1 looking in the direction of arrows A—A.
Figure 2B:
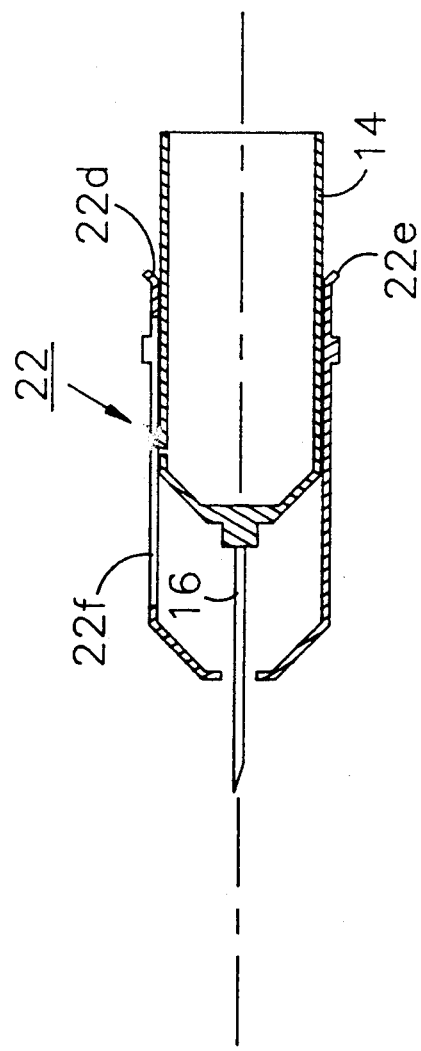
FIG. 2b shows the members of FIG. 2a in the partially assembled position.

FIGS. 1 and 2 show exploded views of the apparatus 10 embodying the principles of the present invention and comprising a disposable hypodermic syringe needle assembly 12 used in hospital and healthcare applications and the like. The syringe includes a cylindrical chamber 14 with a tapered forward end 14a which is typically releasably joined to a hollow hypodermic needle 16 which communicates with the hollow interior of cylindrical body 14.

An integral guide tab 14b extends radially outwardly from cylindrical body 14. A substantially U-shaped slot 14c is provided in cylindrical body 14 to form a flexible projection 14d having guide tab 14b at the end thereof.

Figure 3:
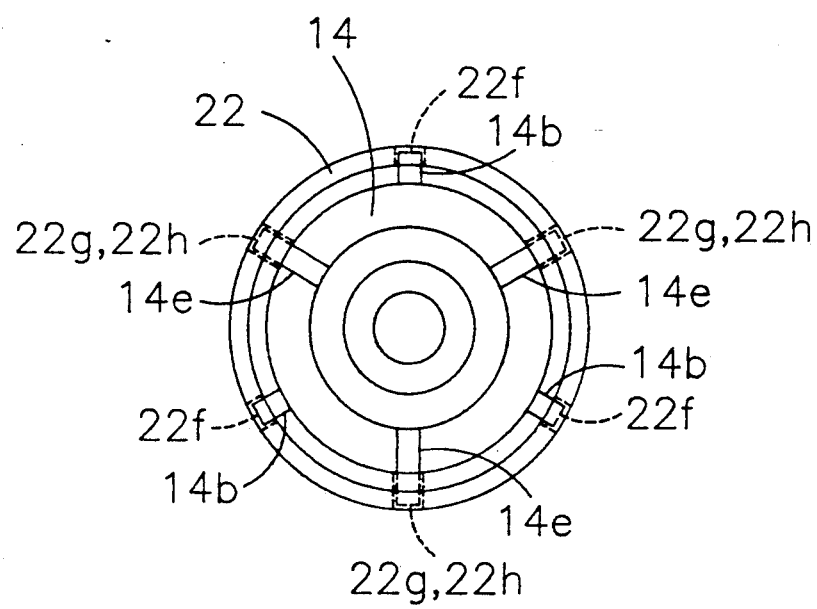
FIG. 3 is a schematic end view of the needle assembly and telescoping shield showing the manner in which the guide track and guide tabs and the locking tabs and mating slots are arranged.

In the preferred embodiment three guide tabs 14b and three guide slots 22f are provided at 120° intervals as shown in schematic fashion in FIG. 3. Only one locking tab and pair of mating slots will be described for purposes of simplicity, it being understood that all three sets of tabs and mating slots operate in similar fashion.

A telescoping shield 20 is adapted to be slidably received upon cylindrical body 14 and has a generally cylindrical-shaped main body portion 22 having a forward tapered end 22a generally conforming to the tapered forward end 14a of the hypodermic syringe assembly 12. The forward end of the tapered portion is truncated and is provided with an opening 22b (note, for example, FIG. 4a) having a diameter sufficient to permit needle 16 to extend therethrough when the telescoping shield 20 is moved to the needle exposing position, as will be more fully described hereinbelow.

Body 22 is provided with open rearward 22c for receiving the forward tapered end of the hypodermic needle assembly 12. An elongated guide slot 22f is provided in body 22 and is substantially parallel to the longitudinal axis A of the body 22. The interior surface of body 22 is provided with a bevelled edge 22d terminating in a lip 22e.

FIG. 4a shows assembly 12 and shield 20 in the disassembled position. In order to assemble these components, the assembly 12 and shield 20 are oriented along a common longitudinal axis A. The shield 20 is then pushed onto the assembly 22. The bevel 22d facilitates the mounting of shield 20 onto assembly 12. Tracking tab 14b is provided with a bevelled surface 14b-1 (see FIG. 1) which cooperates with the bevelled surface 22d to press the locking tab inwardly as the assembly 12 is telescopingly received within shield 20. The flexible projection 14d yields sufficiently to enable the tab 14b to move generally in the inward radial direction. Ultimately, the assembly 12 is pushed into shield 20 to a depth sufficient to move tab 14d into the right-hand end of slot 22f, at which time the yieldable projection 14d causes tab 14b to snap outwardly and into slot 22f shown best in FIGS. 1 and 2b.

Although the shield 20 may be moved linearly relative to assembly 12, tracking tab 14b which, is slidably received within slot 22f, prevents shield 20 from rotating about longitudinal axis A relative to assembly 12.

Noting FIG. 2, shield 20 is provided with a pair of positioning openings 22g and 22h lying along a common imaginary line substantially parallel to longitudinal axis A. The openings 22g and 22h are arranged along the cylindrical body 22 at an angle displaced from elongated slot 22f. For example, the assembly 12 and shield 20 are rotated an angle of 60 degrees from FIG. 1 to FIG. 2 in order to respectively expose the tracking tab 14b and tracking slot 22f in FIG. 1 and the locking tab 14b and mating slots 22g and 22h in FIG. 2.

As shown in FIG. 3, there are preferably three pairs of mating openings 22g, 22h arranged at 120° intervals about shield 20. These three pairs of slots cooperate with three locking tabs 14e arranged at 120° intervals about body 14. Only one tab and its associated pair of openings will be described for purposes of simplicity, it being understood that the remaining tabs and cooperating pairs of openings operate in a similar fashion. The guide tabs and slots are preferably arranged at an angle of 60° from the adjacent locking tabs and cooperating mating openings.

As shown schematically in FIG. 3, it should be understood that the present invention preferably provides three tracking slots 22f arranged at 120 degree intervals about body 22 and three sets of mating slots 22g, 22h arranged at 120 degree intervals about body 22 and further arranged so that they are equally spaced from the intervals along which the tracking slots 22f are provided. Preferably, each pair of mating slots 22g, 22h is displaced an angle of 60 degrees from an adjacent tracking slot 22f.

Body 14 is further provided with three locking tabs 14e, one of which is shown in FIG. 2. Locking tab 14e is integral with body 14 and is flexible to enable the locking tab to be bent into a curved linear shape as will be more fully described hereinbelow. As was set forth hereinabove, there are preferably three such locking tabs arranged at 120 degree intervals about body 14 each locking tab cooperating with a pair of mating slots 22g, 22h, there being three such sets of mating slots 22g, 22h arranged at 120 degree intervals about body 22.

FIG. 4a shows a sectional view of the assembly 12 and shield 20 looking in the direction of arrows B—B of FIG. 2. As was mentioned hereinabove, shield 20 is mounted upon assembly 12 by aligning both of these assemblies along the common longitudinal axis A as shown in FIG. 4a. FIG. 4b shows shield 20 mounted upon assembly 12 with the shield in the needle shielding position. As the shield 20 is pushed from the position shown in FIG. 4a to the position shown in FIG. 4b, each of the locking tabs 14e engages the bevelled interior edge 22d (see FIG. 4a) causing the locking tab to bend downwardly and toward the right relative to FIG. 4b. The locking tab 14e remains in its bent position as it slides along bevelled interior edge 22d and the adjacent interior surface of body 22 until the locking tab moves into mating slot 22h at which time the locking tab snaps into the mating opening 22h and assumes its normal, unbent position 14e shown in FIG. 4b. At this time, the needle 16 is completely shielded by the body 22 to prevent either accidental or even deliberate contact with the needle 16 and especially with the extremely sharp point 16a of needle 16. The open end 22b of shield 22 is preferably covered with a tear-away strip 24 which may, for example, have a pressure sensitive adhesive along its right-hand surface relative to FIG. 4b for engaging the marginal surface surrounding opening 22b to protect the interior region of body 22 and especially needle 16 from being contaminated with foreign material, dirt, dust and the like. Cover sheet 24 is preferably provided with a small tab 24a (see FIG. 2) to facilitate peeling away of the cover sheet 24 from opening 22b.

The shield 20 is moved from the position shown in FIG. 4b to the position shown in FIG. 4c to fully expose needle 16 to facilitate the use of the hypodermic syringe.

The protective cover strip 24 is preferably removed preparatory to moving telescoping shield 20 to expose the needle 16. The shield is moved from the position shown in FIG. 4b to the position shown in FIG. 4c by pushing the shield toward the right relative to assembly 12 as shown in FIG. 4c, causing each of the flexible locking tabs 14e to be bent so that their free ends move downwardly and toward the right. The bent locking tab slides against the interior surface of telescoping shield 22 until each of the tabs move into an associated mating slot 22g at which time the locking tab snaps back to its unbent position and extends into the associated opening 22g in the manner shown best in FIG. 4c. At this time, the needle 16 is fully exposed and the hypodermic syringe assembly 12 is ready for normal use.

In order to prepare the hypodermic needle assembly 12 for disposal, the needle assembly 12 is pulled out of the telescoping shield from the position shown in FIG. 4c to the position shown in FIG. 4d causing each of the locking tabs 14e to bend in the reverse direction, i.e. downwardly and toward the left, as shown in FIG. 4d.

The telescoping shield 20 is moved until it reaches the position shown in FIG. 4d at which time the locking tab snaps outwardly over its free end 14e-1 to rest against shoulder 22j arranged between the main portion of body 22 and the portion 22k of body 22 which is of slightly greater diameter than the main body portion. The telescoping shield is prevented from being pulled any further toward the left relative to the assembly 12 thereby maintaining each of the locking tabs 14e in the flexed position shown in FIG. 4d with the tip of each locking tab resting against shoulder 22j. Any effort to push shield 20 toward the right relative to assembly 12 as shown in FIG. 4d is prevented by the flexed locking tabs 14e which are now in the locked position. Thus, the needle 16 and especially its sharp point 16a is fully surrounded by shield 20 to prevent either accidental or deliberate contact with the needle point enabling the syringe assembly 12 and its cooperating telescoping shield 20 to be safely disposed of.

Although the preferred embodiment of the present invention utilizes three locking tabs and operating mating slots arranged at 120 degree intervals and further utilizes cooperating tracking tabs and tracking slots arranged at 120 degree intervals which are displaced from the locking tabs and cooperating mating slots, a greater or lesser number of such arrangements may be used, for example, as few as one locking tab and cooperating mating slots and as few as one tracking tab and cooperating tracking slot may be employed, if desired.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein described.

What is claimed is:

1. A hypodermic needle and syringe assembly comprising a substantially annular body portion having a forward end for supporting a hypodermic needle;
   a hollow annular shield for telescopingly receiving said needle and body portion;
   said shield being a hollow shell provided with an elongated tracking slot;
   the body of said needle and syringe assembly having an integral flexible tracking tab extending outwardly from said body and being slidably received in said tracking slot when said syringe assembly body is telescopingly received within said shield to prevent relative rotation between said syringe assembly body and said shield;
   said syringe assembly body having an integral flexible locking tab extending outwardly from said body;
   said shield having a pair of mating slots arranged along an imaginary line substantially parallel to the longitudinal axis of said shield and displaced a predetermined angular distance about said shield from said tracking slot;
   said locking tab being bent so that its free end is positioned closer to the surface of said syringe assembly body when said locking tab engages the interior surface of said shield;
   said locking tab snapping into one of said mating slots when coaligned therewith;
   said mating slots being so positioned along the longitudinal axis of said shield whereby said shield completely encloses the needle when said locking tab is positioned in one of said cooperating slots and said syringe assembly body being substantially fully telescoped within said shield to substantially fully expose said needle and especially the free, pointed end thereof when said locking tab is positioned within the remaining one of said mating slots.

2. The apparatus of claim 1 wherein said shield is further provided with an internal shoulder adjacent one of said mating slots for receiving and positioning said locking tab whereby said locking tab is bent in a direction to prevent said shield from being moved in a direction to expose said needle to thereby protect anyone handling the assembly from being damaged from said needle and to thereby permit safe disposal of said assembly.

3. The apparatus of claim 2 wherein said one of said mating slots is provided with a stop adjacent the open end of said shield to prevent the locking tab from being moved from the locking position.

4. The apparatus of claim 1 wherein said shield is further provided with an opening for permitting said needle to extend through said shield when said syringe body is fully telescoped within said shield.

5. The apparatus of claim 4 further comprising seal means for releasably sealing said opening said seal means being removable to uncover said opening.

6. The apparatus of claim 5 wherein said seal means comprises a strip having a pressure sensitive adhesive for releasably adhering to the marginal portion of said shield surrounding said opening.

7. The apparatus of claim 6 wherein said strip comprises a tab extending outwardly from the main portion thereof to facilitate removal of said tab from said shield.

8. A hypodermic needle and syringe assembly comprising a substantially annular body portion having a forward end for supporting a hypodermic needle;
   a hollow annular shield for telescopingly receiving said needle and body portion;
   said shield being a hollow shell provided with a plurality of elongated tracking slots arranged at spaced intervals about said shell;
   the body of said needle and syringe assembly having a plurality of integral flexible tracking tabs arranged at spaced intervals about said body and extending outwardly from said body, each being slidably received in an associated tracking slot when said syringe assembly body is telescopingly received within said shield to prevent relative rotation between said syringe assembly body and said shield;
   said syringe assembly body having an integral flexible locking tab extending outwardly from said body;
   said shield having a pair of mating slots arranged along an imaginary line substantially parallel to the longitudinal axis of said shield and displaced a predetermined angular distance about said shield from said tracking slot;
   said locking tab being bent so that its free end is positioned closer to the surface of said syringe assembly body when said locking tab engages the interior surface of said shield;
   said locking tab snapping into one of said mating slots when coaligned therewith;
   said mating slots being so positioned along the longitudinal axis of said shield whereby said shield completely encloses the needle when said locking tab is positioned in one of said cooperating slots and said syringe assembly body being substantially fully telescoped within said shield to substantially fully expose said needle and especially the free, pointed end thereof when said locking tab is positioned within the remaining one of said mating slots.

9. The apparatus of claim 8 wherein the tracking slots and three tracking tabs are provided respectively at 120° intervals about said shell and about said body.

10. A hypodermic needle and syringe assembly comprising a substantially annular body portion having a forward end for supporting a hypodermic needle;
a hollow annular shield for telescopingly receiving said needle and body portion;
said shield being a hollow shell provided with an elongated tracking slot;
the body of said needle and syringe assembly having an integral flexible tracking tab extending outwardly from said body and being slidably received in said tracking slot when said syringe assembly body is telescopingly received within said shield to prevent relative rotation between said syringe assembly body and said shield;
said syringe assembly body having a plurality of integral flexible locking tabs arranged at spaced intervals about said body and extending outwardly from said body;
said shield having a plurality of pairs of mating slots each pair being arranged along an imaginary line substantially parallel to the longitudinal axis of said shield and displaced a predetermined angular distance about said shield from said tracking slot, said imaginary lines being arranged at spaced intervals about said body;
said locking tabs being bent so that their free ends are positioned closer to the surface of said syringe assembly body when said locking tab engages the interior surface of said shield;
said locking tabs snapping into one of said mating slots when coaligned therewith;
said mating slots being so positioned along the longitudinal axis of said shield whereby said shield completely encloses the needle when said locking tab is positioned in one of said cooperating slots and said syringe assembly body being substantially fully telescoped within said shield to substantially fully expose said needle and especially the free, pointed end thereof when said locking tab is positioned within the remaining one of said mating slots.

11. The apparatus of claim 10 wherein three locking tabs and three pairs of mating openings are respectively provided at 120° intervals about said body and said shell.

* * * * *